US009557394B2

(12) United States Patent
Espy et al.

(10) Patent No.: US 9,557,394 B2
(45) Date of Patent: *Jan. 31, 2017

(54) CLASSIFICATION OF MATERIALS USING NUCLEAR MAGNETIC RESONANCE DISPERSION AND/OR X-RAY ABSORPTION

(71) Applicant: Los Alamos National Security, LLC, Los Alamos, NM (US)

(72) Inventors: Michelle A. Espy, Los Alamos, NM (US); Andrei N. Matlashov, Los Alamos, NM (US); Larry J. Schultz, Los Alamos, NM (US); Petr L. Volegov, Los Alamos, NM (US); Algis Urbaitis, Albuquerque, NM (US); Henrik Sandin, Los Alamos, NM (US); Jacob Yoder, Los Alamos, NM (US); Stephen Surko, Chevy Chase, MD (US)

(73) Assignee: U.S. Department of Energy, Washington, DC (US)

( * ) Notice: Subject to any disclaimer, the term of this patent is extended or adjusted under 35 U.S.C. 154(b) by 869 days.

This patent is subject to a terminal disclaimer.

(21) Appl. No.: 13/869,705

(22) Filed: Apr. 24, 2013

(65) Prior Publication Data

US 2013/0285657 A1 Oct. 31, 2013

Related U.S. Application Data

(60) Provisional application No. 61/637,983, filed on Apr. 25, 2012.

(51) Int. Cl.
*G01V 3/00* (2006.01)
*G01R 33/44* (2006.01)
(Continued)

(52) U.S. Cl.
CPC .............. *G01R 33/44* (2013.01); *G01N 24/084* (2013.01); *G01R 33/4812* (2013.01)

(58) Field of Classification Search
CPC .................................................. G01R 33/4812
(Continued)

(56) References Cited

U.S. PATENT DOCUMENTS

| 4,390,840 A | 6/1983 | Ganssen |
| 5,596,195 A | 1/1997 | Obori et al. |

(Continued)

FOREIGN PATENT DOCUMENTS

WO WO 2008008447 1/2008

OTHER PUBLICATIONS

Bodurka, et al., Toward Direct Mapping of Neuronal Activity: MRI Detection of Ultraweak, Transient Magnetic Field Changes; 47 Magnetic Resonance in Medicine, pp. 1052-1058 (2002).

(Continued)

*Primary Examiner* — Louis Arana
(74) *Attorney, Agent, or Firm* — Lewis Roca Rothgerber Christie LLP

(57) ABSTRACT

Methods for determining the identity of a substance are provided. A classification parameter set is defined to allow identification of substances that previously could not be identified or to allow identification of substances with a higher degree of confidence. The classification parameter set may include at least one of relative nuclear susceptibility (RNS) or an x-ray linear attenuation coefficient (LAC). RNS represents the density of hydrogen nuclei present in a substance relative to the density of hydrogen nuclei present in water. The extended classification parameter set may include $T_1$, $T_2$, and/or $T_{1\rho}$ as well as at least one additional classification parameter comprising one of RNS or LAC. Values obtained for additional classification parameters as (Continued)

well as values obtained for $T_1$, $T_2$, and $T_{1\rho}$ can be compared to known classification parameter values to determine whether a particular substance is a known material.

18 Claims, 7 Drawing Sheets

(51) Int. Cl.
*G01R 33/48* (2006.01)
*G01N 24/08* (2006.01)

(58) Field of Classification Search
USPC .......................................... 324/300, 306, 309
See application file for complete search history.

(56) References Cited

U.S. PATENT DOCUMENTS

| | | | |
|---|---|---|---|
| 5,804,967 | A | 9/1998 | Miller |
| 6,577,125 | B2 | 6/2003 | Prammer |
| 6,674,282 | B2 | 1/2004 | Pines |
| 6,675,106 | B1 | 1/2004 | Keenan et al. |
| 7,059,524 | B2 | 6/2006 | Knowles |
| 7,061,237 | B2 | 6/2006 | Pines |
| 7,187,169 | B2 | 3/2007 | Clarke |
| 7,251,310 | B2 | 7/2007 | Smith |
| 7,394,250 | B2 | 7/2008 | Itozaki |
| 7,397,241 | B2 | 7/2008 | Gauthausen |
| 7,541,806 | B2 | 6/2009 | Appelt |
| 7,573,268 | B2 | 8/2009 | Volegov et al. |
| 7,688,069 | B2 | 3/2010 | Kraus, Jr. |
| 7,729,740 | B2 | 6/2010 | Kraus, Jr. et al. |
| 7,764,764 | B2 | 7/2010 | Harding |
| 2005/0270026 | A1 | 12/2005 | Guthausen |
| 2006/0273786 | A1 | 12/2006 | Smith |
| 2007/0063700 | A1 | 3/2007 | Levitt |
| 2008/0074113 | A1 | 3/2008 | Clarke |
| 2008/0284433 | A1 | 11/2008 | Kraus, Jr. et al. |
| 2009/0206269 | A1 | 8/2009 | Kraft et al. |
| 2009/0289629 | A1 | 11/2009 | Tuchman |
| 2013/0072780 | A1 | 3/2013 | Espy |
| 2013/0317758 | A1* | 11/2013 | Espy .............. G01R 33/44 702/28 |
| 2014/0270066 | A1* | 9/2014 | Magnuson ..... G01R 33/4812 378/62 |

OTHER PUBLICATIONS

Espy, et al., SQUID-Based Simultaneous Detection of NMR and Biomagnetic Signals at Ultra-Low Magnetic Fields; IEEE Transactions on Applied Superconductivity, vol. 15, No. 2, Jun. 2005, pp. 635-639.

Espy, et al., Ultra-low Field MRI for the Detection of Liquid Explosives Using SQUIDs; IEEE/CSC & ESAS European Superconductivity News Forum, No. 9, Apr. 2009, pp. 1-12.

Matlachov, et al., SQUID detected NMR in microtesla magnetic fields; Journal of Magnetic Resonance, 170 (2004) pp. 1-7.

McDermott, et al., Liquid-State NMR and Scalar Couplings in Microtesla Magnetic Fields; Science Mar. 22, 2002, pp. 2247-2249.

Xiong, et al., Directly Mapping Magnetic Field Effects of Neuronal Activity by Magnetic Resonance Imaging; Human Brain Mapping, vol. 20, pp. 41-49 (2003).

* cited by examiner

CLASSIFICATION OF MATERIALS USING NUCLEAR MAGNETIC RESONANCE DISPERSION AND/OR X-RAY ABSORPTION

CLAIM OF PRIORITY

The present application claims the benefit of U.S. Provisional Patent Application Ser. No. 61/637,983 filed on 25 Apr. 2012 and entitled "Classification of Materials Using Magnetic Resonance Dispersion and/or X-Ray Absorption," the entirety of which is incorporated herein by this reference.

STATEMENT REGARDING FEDERAL RIGHTS

This invention was made with government support under Contract No. DE-AC52-06NA25396, awarded by the U.S. Department of Energy to Los Alamos National Security, LLC for the operation of the Los Alamos National Laboratory. The government has certain rights in the invention.

BACKGROUND

The identity of unknown substances can be determined through a variety of means. When samples of an unknown substance can be obtained, various tests and analyses can be performed to determine the likely identity of the substance. In some instances, however, it is either not possible or not desirable to obtain samples of an unknown substance. In such cases, non-invasive methods of material analysis are preferred.

For example, in security settings, efficiency concerns dictate use of non-invasive identification techniques such as x-ray analysis. More recently, nuclear magnetic resonance (NMR) has been used in security settings to identify unknown substances by measuring common NMR parameters and comparing these parameter values to known parameter values of known substances. In some instances, however, the measured NMR parameter values are not sufficient to positively identify an unknown substance. Current NMR analysis techniques can also be too time intensive to be useful in high-throughput security settings.

SUMMARY OF THE PRESENT INVENTION

A variety of technologies for analyzing measurement data, determining classification parameter values, and identifying substances are provided. The technologies can be used, for example, to non-invasively determine the identity of a substance.

Nuclear magnetic resonance (NMR) technology has recently been applied to determine the identity of substances by obtaining values for NMR relaxation parameters $T_1$, $T_2$, and $T_{1\rho}$ and comparing these parameter values to known parameter values for known materials. In many cases, however, multiple materials have similar values for $T_1$, $T_2$, and $T_{1\rho}$, making it difficult to distinguish both hazardous materials from non-hazardous materials and different hazardous materials from each other based on the NMR relaxation parameters alone.

As described herein, an extended classification parameter set is defined to allow identification of substances that previously could not be identified or to allow identification of substances with a higher degree of confidence. An extended classification parameter set may include at least one of relative nuclear susceptibility (RNS) or an x-ray linear attenuation coefficient (LAC). RNS represents the density of hydrogen nuclei present in a substance relative to the density of hydrogen nuclei present in water. The extended classification parameter set may include $T_1$, $T_2$, and/or $T_{1\rho}$ as well as at least one additional classification parameter comprising one of RNS or LAC. Values obtained for additional classification parameters as well as values obtained for $T_1$, $T_2$, and $T_{1\rho}$ can be compared to known classification parameter values to determine whether a particular substance is a known material.

Classification parameter values are obtained by performing measurements, and these measurements have a cost in required energy, result processing, time, and other resources. The technologies provided herein include hypothesis-driven methods of performing measurements in efficient number and order to identify a substance with a low overall measurement cost. For example, based on determined measurement costs for a variety of measurement techniques and/or initial probabilities that materials in a reference group will be encountered, optimized or efficient measurement sequences can be determined such that the substance being analyzed can be identified by performing a smaller number of measurements than if measurements were performed in an arbitrary manner.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS

Figure 1:
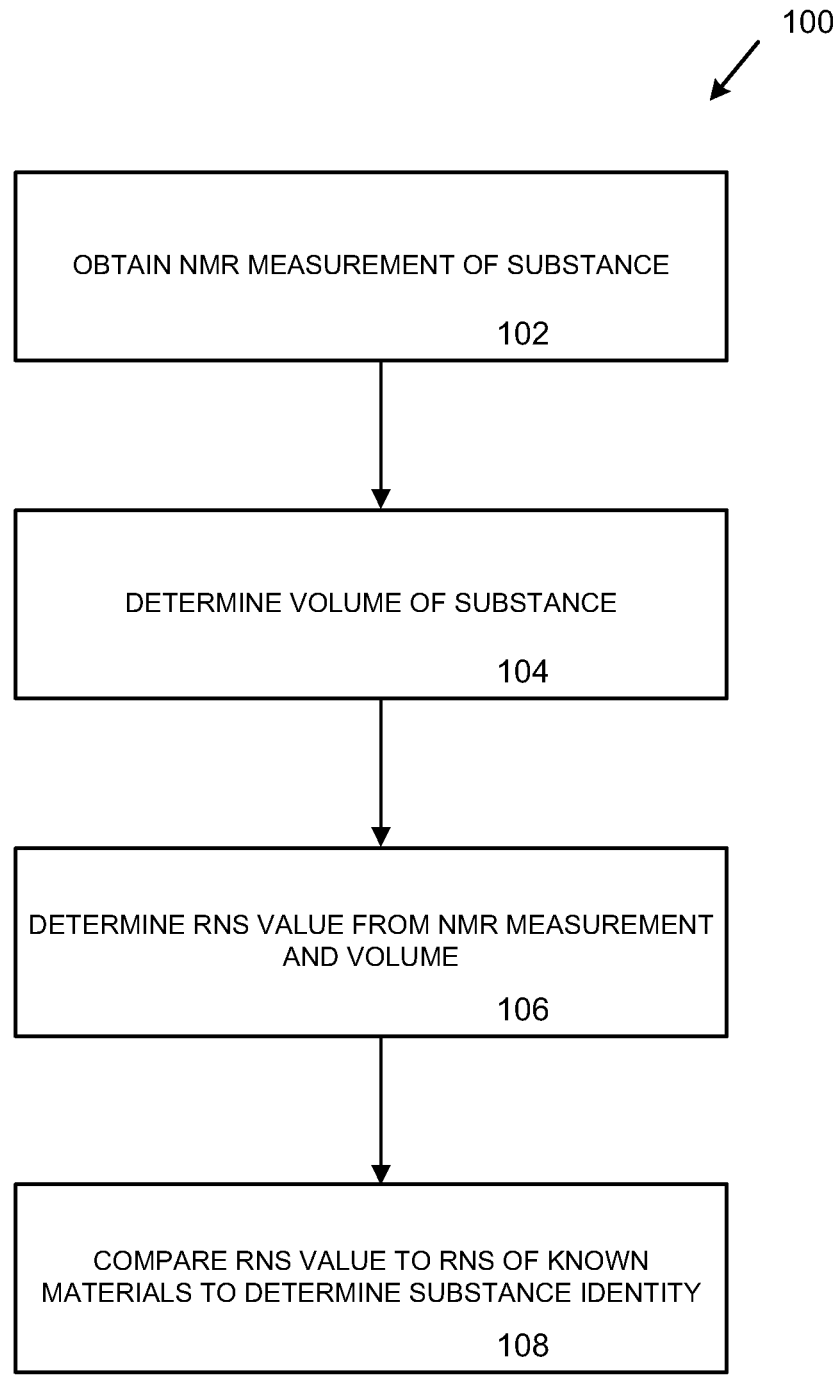
FIG. 1 is a flowchart depicting an example method for identifying a substance in which RNS values are compared.

As a person skilled in the art will recognize from the following detailed description and from the figures and claims, modifications and changes can be made to the preferred embodiments of the invention without departing from the scope of this invention defined in the following claims.

In the techniques and solutions described herein, methods for determining the identity of a substance are provided. As discussed above, use of the relaxation parameters $T_1$, $T_2$, and $T_{1\rho}$ measured via ultra-low field nuclear magnetic resonance methods, has recently been accomplished for the purpose of material classification. See U.S. Pat. No. 7,688,069, issued Mar. 30, 2010, titled "Ultra-Low Field Nuclear Magnetic Resonance and Magnetic Resonance Imaging to Discriminate and Identify Materials."

Extended Classification Parameters

Improved performance in material classification may be achieved by the integration of additional information to the $T_1$, $T_2$, and/or $T_{1\rho}$ set, relative to using $T_1$, $T_2$, and $T_{1\rho}$ alone. Additional classification parameters may include relative nuclear susceptibility (RNS) and X-ray linear attenuation coefficient (LAC), at single or multiple X-ray energies. Alternatively, these additional classification parameters (including RNS and/or LAC) may be used to classify materials without $T_1$, $T_2$, and/or $T_{1\rho}$. (As used herein, material classification and substance identification are synonymous.)

Relative Nuclear Susceptibility

Volume nuclear susceptibility relates the magnetization (M) of a substance S to the strength of an applied magnetic field (H) per $$M = x_v \cdot H$$

Relative nuclear susceptibility (RNS) is obtained simply as the ratio of susceptibility of a particular substance to the susceptibility of a reference sample (we will assume we reference the susceptibility of water, Xw) per $$RNS_s = Xs/Xw$$

Magnetization in a material arises due to the polarization of spins present in isotopes that contain an odd number of protons and/or neutrons. For practical purposes, in common materials, the signal comes from hydrogen nuclei. Therefore, RNS is a measure of the density of hydrogen nuclei present in a material relative to the density of hydrogen nuclei present in water.

RNS is thus a powerful parameter for material classification because different substances have different hydrogen content.

X-Ray Linear Attenuation Coefficient

X-rays passing through a material will be attenuated by interaction with the electron cloud of the material. If an X-ray beam at nominal energy E, of intensity I0, passes through a thickness L of substance S, then the outgoing intensity of the beam, I, may be expressed as $$I = I_o e^{-\lambda_E L},$$

where $\lambda_E$ is the linear attenuation coefficient (LAC) of the material at energy E.

Different substances exhibit different LAC, and the relationship of LAC to beam energy differs between substances. LAC is therefore a parameter that can be used to classify materials.

Example Extended Parameter Set

An exemplary extended parameter dataset is as follows:

$$D = [T_1, T_2, T_v, RNS, LAC],$$

Here, LAC contains measurements at one or more X-ray energies. (Bold font denotes vectors and matrices.) Other exemplary extended parameter datasets may contain RNS but not LAC or vice-versa. Additional classification parameters not disclosed herein are also contemplated.

Measurement of the full set of parameters D can result in more efficient material classification than any subset of these parameters. In other words, for some pair of substances A and B, it may not be possible to identify or distinguish between A and B with LAC only, RNS only, or $T_1$, $T_2$, and/or $T_{1\rho}$ only (with a desired degree of confidence). Inclusion of more classification parameters in the set of parameters being used (measuring a greater portion of D or the full D) can allow identifying or distinguishing A and B with the desired degree of confidence.

Measuring the Parameters $T_1$ and $T_2$ can be measured as described in U.S. Pat. No. 7,688,069. Measuring LAC is well described in the public domain, but in some examples of the technology described herein, X-ray LAC and ULF (ultra-low frequency)-NMR parameters are measured using the same instrument. Two exemplary methods for measuring RNS are set forth below.

In a ULF-NMR measurement, signal amplitude is proportional to nuclear susceptibility (because hydrogen nuclei make the signal, and nuclear susceptibility is proportional to the density of hydrogen nuclei). To measure RNS, we can measure the signal amplitude $A_s$ arising from a volume of substance S. We can also measure the signal $A_w$ from the same volume of water. RNS can then be defined as:

$$RNS_s = A_s/A_w$$

However, signal amplitude is also dependent on the volume of material present. In order to measure RNS for an arbitrary volume the amplitude signal must be normalized for volume. Two exemplary methods for accomplishing this are presented below.

Example Volume Determination Method 1: Multiple NMR Sensors

The NMR signal may be measured with an inductive pickup coil. Magnetization in a volume near to such a coil will induce a measureable proportional current in the coil. Such pickup coils are well described in the public domain. A smaller volume of material would produce a lower signal strength. A material with lower RNS would also produce a lower signal strength.

Alternative, another pickup coil (coil 2) can be added inside coil 1. In this case, a smaller RNS will produce a lower signal strength in both coils. However, a smaller volume will produce a larger drop in coil 1's signal than in coil 2's signal, because each coil is sensitive to material very near it. The ratio of signal from one coil to the other is indicative of material volume. This volume estimate is then used to normalize the amplitude signal and thus have sensitivity to RNS.

A concentric arrangement of two or more pickup coils or other magnetic sensors as described above can thus be used to disambiguate volume from RNS and thus measure RNS for an arbitrary volume of material.

Example Volume Determination Method 2: X-Ray Image

In this method, an X-ray image of the substance volume can be obtained. The X-ray image can be used to compute sample volume. This information can be used to normalize for volume and thus measure RNS.

Example Substance Identification Method 1

An exemplary method 100 for determining the identity of a substance is illustrated in FIG. 1. Method 100 can be implemented at least in part by a computing device. In step 102, an ultra-low field nuclear magnetic resonance (NMR) measurement of a substance is obtained. In step 104, a volume of the substance is determined. Volume determination may be accomplished through either the "multiple MNR sensors" (concentric coil) or "X-ray image" methods discussed above or through other methods. In some examples where the concentric coil method is used, volume is determined at least in part through analysis of current induced in each of two substantially concentric coils in response to magnetization of the substance. The analysis may comprise determining a ratio of the current induced in a first of the two substantially concentric coils and the current induced in a second of the two substantially concentric coils. The determined ratio is indicative of the volume of the substance.

An RNS value is determined in step 106 based at least in part on the obtained NMR measurement and the determined volume. The determined RNS value for the substance is compared to RNS values of known materials in a reference group to determine whether the substance is one of the known materials in step 108.

In some examples, step 108 includes searching a list of known materials and corresponding RNS values. The known materials in the reference group may be hazardous materials, and the method 100 may be directed to identify hazardous substances non-invasively (such as in airport security or other high-throughput scenarios). In other examples, method 100 may further comprise outputting a result, and the result may be one of an identification of the substance as a known material in the reference group or a determination that the substance is not one of the known materials in the reference group. The result can also comprise an indication of a degree of confidence in the identification (e.g. an indication such as high, medium, low, a percentage indication such as 0-100%, or other type of indication). The result can also comprise relative confidences, such as a list of materials with the most probably match listed first.

In method 100, RNS is used to identify a substance. As discussed above, other classification parameters such as $T_1$, $T_2$, $T_{1\rho}$, and/or LAC can be used in conjunction with RNS to achieve identification more accurately or more quickly.

Example Substance Identification Method 2

Figure 2:
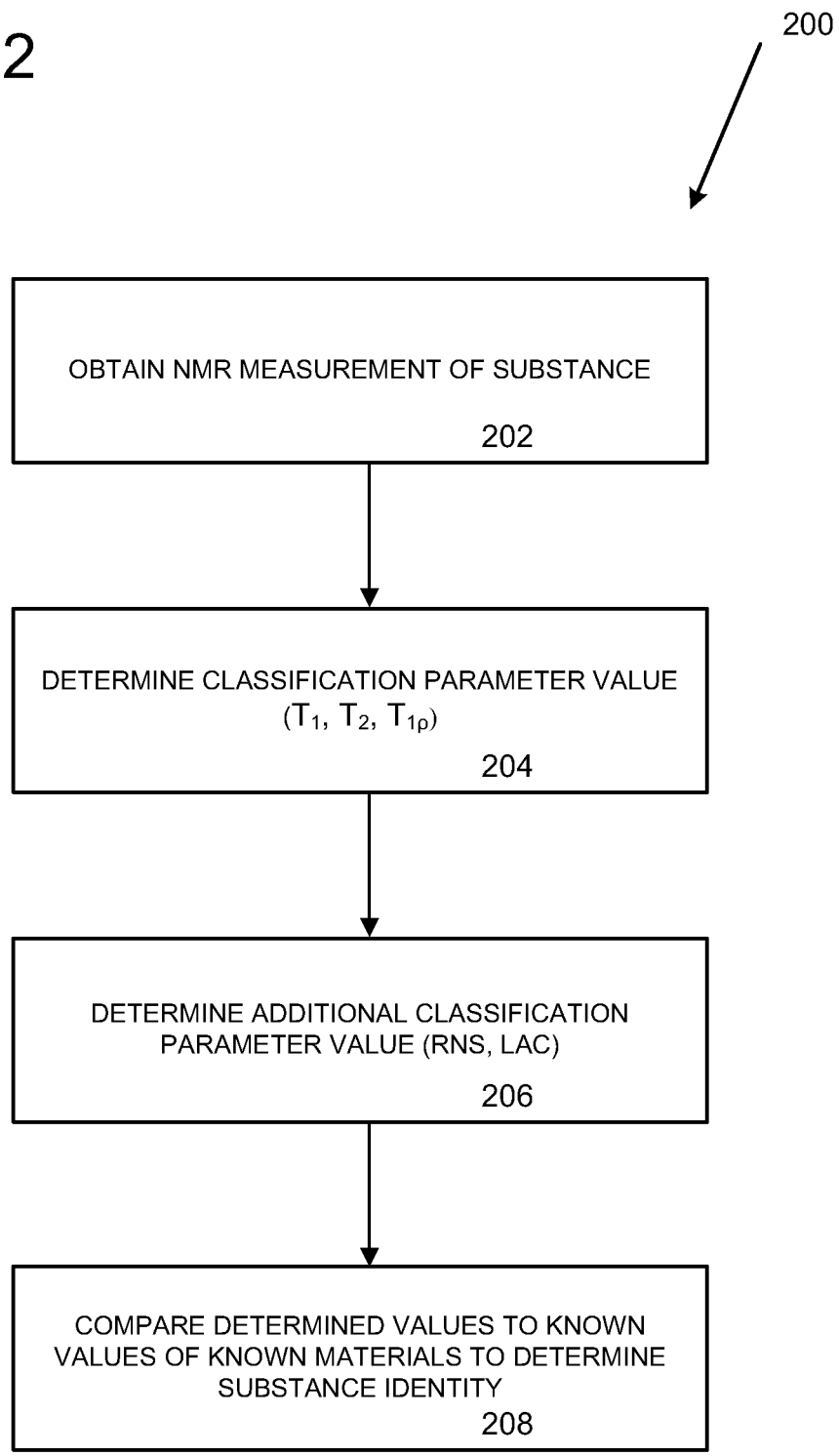
FIG. 2 is a flowchart depicting an example method for identifying a substance in which classification parameter values and additional classification parameter values are compared.

An exemplary method 200 for determining the identity of a substance is illustrated in FIG. 2. Method 200 may be implemented at least in part by a computing device. In step 202, an ultra-low field nuclear magnetic resonance (NMR) measurement of a substance is obtained. The NMR measurement is analyzed in step 204 to determine a value of at least one of classification parameters $T_1$, $T_2$, and $T_{1\rho}$. In step 206, a value of at least one additional classification parameter is determined. The at least one additional classification parameter comprises one of RNS or LAC. In step 208, the values of the at least one classification parameter and the at least one additional classification parameter are compared to classification parameter values of known materials in a reference group to determine whether the substance is one of the known materials. Similar additional features as discussed with reference to example 1 may be present in example 2 as well.

B. Hypothesis-Driven Scanning Sequences for Classification of Materials

As discussed above, an exemplary classification parameter dataset can be defined as $$D=[T_1,T_2,RNS,LAC].$$

A database of materials $\{M_i\}$ to be detected can be defined as a collection of statistical properties of the exemplary classification parameters D of the materials. Such statistical properties can be defined as, for example, conditional probability densities of classification parameters:

$$\{P(T_1,T_2,RNS,LAC|M_i)\}$$

An example of such conditional probability is a multivariate normal distribution:

$$P(T_1,T_2,RNS,LAC|M_i)=P(D|M_i)=(2\pi)^{-k/2}|C_i|^{-1/2}\exp\{-(D-D_i)^T C_i^{-1}(D-D_i)\},$$

where $D_i$ is classification data set for $i^{th}$ material, $C_i$ is a covariance matrix for classification parameters, and k is the number of classification parameters.

The measurement cost of each classification parameter is furthermore defined as $W=[W_{T1}, W_{T2}, W_{RNS}, W_{LAC}]$. In some examples, the measurement cost is the time required to measure a parameter with a specified accuracy. In other examples, measurement cost may also reflect required energy, computation resources required, and/or other resources required. Measurement cost may be supplied by a manufacturer of equipment used to perform the measurements or may be determined empirically by a user.

Each material in a group of reference materials is assigned an initial (a priori) probability $P_o$ that the material is the substance being analyzed. The group of reference materials can take the form of a database, table, list, or other structure. The most efficient measurement to perform (MSRM) is selected in such a way that the a posteriori probabilities $P(M_i|MSRM)$ allows the group of reference materials to be triaged into two classes: 1) "plausible" and 2) "eliminated". The "plausible" here means that the substance being analyzed could be one of these materials, the "eliminated" means that the substance being analyzed is not one of these materials. The most efficient measurement here means the measurement with minimal cost (for example, minimum time to complete). The procedure can then be repeated until the "plausible" class contains one entry with the a posteriori probability $P(M_x|MSRM_1, MSRM_2, \ldots MSRM_n)$ greater than a specified detection criteria. Detection criteria (or confidence) can be set by the user.

When a single material in the reference group remains and has an a posteriori probability greater than the specified detection criteria, then the process is stopped, and it can be determined that the substance being analyzed is the single material. If an a posteriori probability greater that the specified detection criteria cannot be achieved, it can be determined that the substance being analyzed is not one of the materials in the reference group. Such a process of determining the identity of a substance (or determining that the substance is not one of a reference group) is thus optimized because measurements are conducted in an order according to which measurement has the highest probability of quickly ascertaining the identity of the substance.

The determination of measurement sequences described above can be thought of as "hypothesis driven" because measurement costs and/or initial probabilities that a known material in a reference group will be encountered are used to form a hypothesis about which measurement will yield the most useful information in the least amount of time (or with the least computational or energy cost). Measurements are then carried out according to the hypothesis (sequence). Examples are presented below for further clarification.

Example 1

Figure 3:
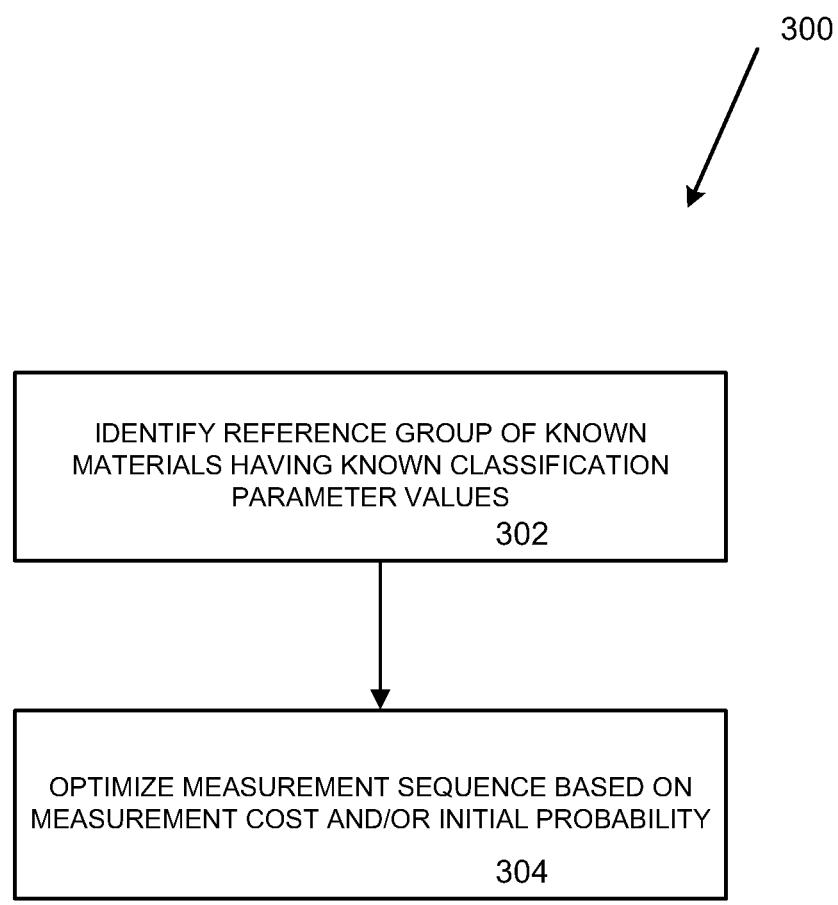
FIG. 3 is a flowchart depicting an example method for identifying a substance in which a measurement sequence is optimized.

An exemplary method 300 for determining the identity of a substance is illustrated in FIG. 3. Method 300 may be implemented at least in part by a computing device. A reference group of known materials is identified in step 302, the known materials having known values for classification parameters. The classification parameters comprise at least one of $T_1$, $T_2$, $T_{1\rho}$, RNS, and LAC. In step 304, a measurement sequence is optimized based on at least one of a measurement cost of the classification parameters and an initial probability of the known materials in the reference group.

In some examples at least one classification parameter value is obtained for the substance according to the optimized measurement sequence. The at least one classification parameter value obtained for the substance may then be compared to classification parameter values of the known materials in the reference group to determine whether the substance is one of the known materials. In some examples, comparison of obtained classification parameter values with known values includes searching a list of the known materials in the reference group and corresponding classification parameter values.

Method 300 can also comprise outputting a result. The result can be one of an identification of the substance as a known material or a determination that the substance is not one of the known materials in the reference group. In some examples, the known materials in the reference group are hazardous materials.

As discussed above, the measurement sequence is optimized in step 304. In some examples, the optimized measurement sequence specifies an order in which measurements to obtain classification parameter values are performed such that classification parameter values sufficient to identify the substance are obtained more quickly than if an alternative measurement sequence were used. Thus, the optimized measurement sequence will achieve measurements more quickly than, for example, always performing measurements in a particular sequence of $T_1$, $T_2$, $T_{1\rho}$, RNS, and then LAC. As discussed above and further explained below, optimization of the measurement sequence depends upon the characteristics of the known materials in the reference group and is thus reference group dependent (initial probabilities of the known materials in the reference group are used in the calculations). (Although, in some examples, an optimized measurement sequence could be determined that considers only measurement cost and does not consider the reference group.) The initial probability of each material in the reference group is the probability of the substance being identified as the material and is established independent of obtaining any classification parameter values for the substance.

In some examples, the optimized measurement sequence is updated upon a first classification parameter value being obtained for the substance and the first classification parameter value being determined to be insufficient to identify the substance at a predetermined confidence level. In other examples, another measurement is obtained according to the original optimized measurement sequence when it is determined that the first classification parameter value is insufficient. As discussed above, the measurement cost of each classification parameter may reflect the time required to obtain a measurement value of the classification parameter.

Example 2

Figure 4:
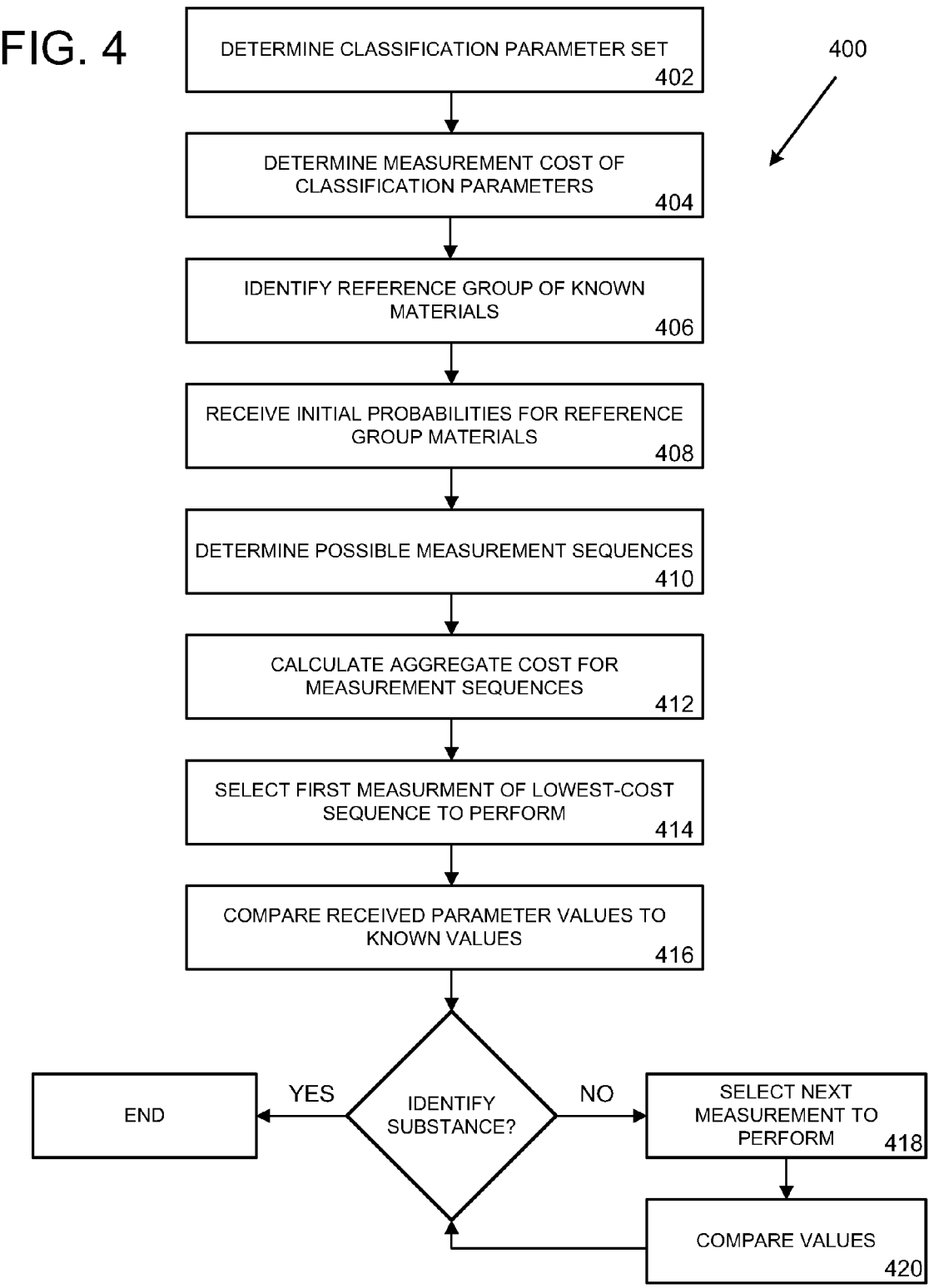
FIG. 4 is a flowchart depicting an example method for identifying a substance in which a measurement sequence is optimized according to aggregate cost of possible measurement sequences.

An exemplary method 400 for determining the identity of a substance is illustrated in FIG. 4. Method 400 may be implemented at least in part by a computing device. In step 402, a set of classification parameters for which values can be obtained is determined. The classification parameters comprise at least one of $T_1$, $T_2$, $T_{1\rho}$, RNS, and LAC. In step 404, a measurement cost of each classification parameter in the set is determined. Measurement cost may relate to the time required to perform the measurement and obtain classification parameter values.

A reference group of known materials each having known classification parameter values is identified in step 406. In step 408, an initial probability is received for each material in the reference group. A plurality of measurement sequences for obtaining values for each of the set of classification parameters for the substance is determined in step 410. An aggregate cost for each of the plurality of measurement sequences is calculated in step 412 based on the determined measurement costs of each classification parameter in the set and the received initial probabilities. In step 414, the first measurement of the measurement sequence having the lowest calculated aggregate cost is selected as the first measurement to perform.

Upon receiving a classification parameter value for the substance resulting from the first measurement to perform, the received classification parameter value is compared to the known classification parameter values of the known materials in the reference group in step 416 to determine whether the substance is one of the known materials. If the substance can be identified at a predetermined confidence level as one of the known materials in the reference group, the method ends. At this point, for example, results of the identification could be output. In step 418, upon determining that the substance cannot be identified at a predetermined confidence level based on the received classification parameter value, a second measurement to perform is selected. Upon receiving a second classification parameter value for the substance resulting from the second measurement to perform, the second received classification parameter value is compared to the known classification parameter values of the known materials in the reference group in step 420 to determine whether the substance is one of the known materials. If the substance can be identified at a predetermined confidence level as one of the known materials in the reference group, the method ends. In some examples, additional measurements are selected until either the substance is identified or all available measurements have been conducted and it can be determined that the substance is not one of the known materials in the reference group.

In some examples, step 418 is implemented by: determining a revised plurality of measurement sequences for obtaining values for each of the set of classification parameters for the substance except the classification parameter for which a value was obtained using the first measurement to perform; calculating an aggregate cost for each of the revised plurality of measurement sequences; and selecting the first measurement of the measurement sequence in the revised plurality of measurement sequences having the lowest calculated aggregate cost as the second measurement to perform. In such examples, possible measurement sequences are thus reevaluated without considering the classification parameter for which a value has already been received. This can be thought of as an iterative optimization each time the substance cannot be identified with the required confidence. In such examples, each of the revised plurality of measurement sequences will be shorter than the original measurement sequences because a previously considered classification parameter is not present in the revised sequences.

Example 3

Figure 5:
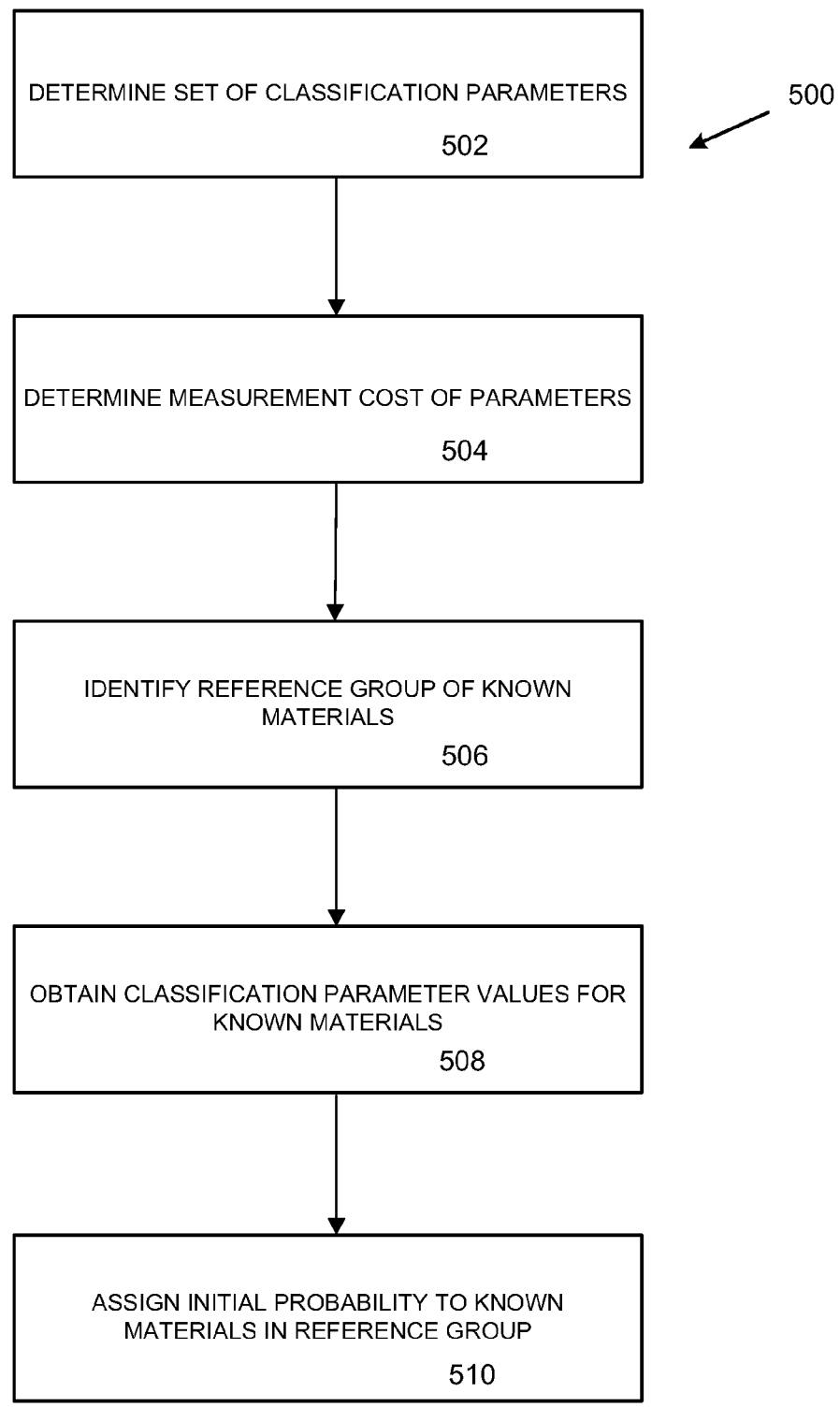
FIG. 5 is a flowchart depicting an example method for building one or more substance identification tables for determining the identity of a substance.

An exemplary method 500 for building one or more substance identification tables for determining the identity of a substance are illustrated in FIG. 5. Method 500 may be implemented at least in part by a computing device. In step 502, a set of classification parameters for which values can be obtained is determined. The classification parameters comprise at least one of $T_1$, $T_2$, $T_{1\rho}$, RNS, and LAC. In step 504, a measurement cost of each classification parameter in the set is determined. The measurement cost reflects the time required to obtain a measurement value of the classification parameter. In step 506, a reference group of known materials is identified. Classification parameter values for each of the known materials in the reference group are obtained in step 508. An initial probability is assigned to each material in the reference group in step 510. Such a substance identification table can be used to identify substances as discussed above with regard to methods 100, 200, 300, 400, and other exemplary methods.

Example Optimization 1

Assume two classification parameters: $x_1$ and $x_2$. The reference group of known materials contains three entries, as shown in the Table 1.

TABLE 1

Reference Group of Known Materials

| Material | Parameter $x_1$ | Parameter $x_2$ | Probability that the material to be tested is this entry |
|---|---|---|---|
| $M_1$ | a | c | $P_1$ |
| $M_2$ | b | c | $P_2$ |
| $M_3$ | a | d | $P_3$ |

The costs of measurement of the parameters $x_1$ and $x_2$ to differentiate a from b and c from d, with the required detection probability Pa are $c_1$ and $c_2$, as summarized in the Table 2.

TABLE 2

Measurement cost

| Measurement | Cost |
|---|---|
| $MSRM_1$, parameter $x_1$ | $c_1$ |
| $MSRM_2$, parameter $x_2$ | $c_2$ |

In this example we have two choices: Measure the parameter $x_1$ first ($MSRM_1$), and then, depending on the outcome, measure or not measure the parameter $x_2$ ($MSRM_2$), or Measure the parameter $x_2$ first ($MSRM_2$), and then, depending on the outcome, measure or not measure the parameter $x_1$ ($MSRM_1$)

To decide which strategy is most efficient we first build a decision diagram (tree) and calculate aggregate (average) measurement cost for the each possible strategy. In this example:

Strategy 1:

Make $MSRM_1$ at cost $c_1$, if the result is b, which will happen in $P_2$ cases, then the material under study is $M_2$, if the result is a, which will happen in $(1-P_2)$ cases, then the material under study is either $M_1$ or $M_3$, to differentiate these materials we do $MSRM_2$ at cost $c_2$. The average cost is then $K_1=P_2 \cdot c_1+(1-P_2)(c_1+c_2)$.

Strategy 2:

Make $MSRM_2$ at cost $c_2$, if the result is d, which will happen in $P_3$ cases, then the material under study is $M_3$, if the result is c, which will happen in $(1-P_3)$ cases, then the material under study is either $M_1$ or $M_2$, to differentiate these materials we do $MSRM_1$ at cost $c_1$. The average cost is then $K_2=P_3 \cdot c_2+(1-P_3)(c_1+c_2)$.

Now the preferred methods can can compare average cost of each approach, i.e. $K_1$ and $K_2$, and choose the most efficient strategy: if $K_1 \leq K_2$, we use the first approach, otherwise we use the second approach. The relationship $K_1 \leq K_2$ is equivalent to $P_3 \cdot c_1 \leq P_2 \cdot c_2$ which allows us to make the decision using entries in the Tables 1 and 2.

The preferred approach is illustrated using several specific cases: (1) $P_2=P_3=P$, $c_1=c_2=c$, in which case $K_1=K_2=c \cdot (2-P)$, therefore the strategies are equivalent and one can choose strategy 1; (2) $P_2=P$, $P_3=2 \cdot P$, $c_1=c_2=c$, in which case $K_1=c \cdot (2-P)$, $K_2=c \cdot (2-2 \cdot P)$, therefore $K_1>K_2$ and one can choose strategy 2 as more efficient; (3) $P_2=P$, $P_3=2 \cdot P$, $c_1=c$, $c_2=2 \cdot c$, in which case $K_1=c \cdot (3-2 \cdot P)$, $K_2=c \cdot (3-2 \cdot P)$, therefore $K_1=K_2$ and one can choose strategy 1.

Example Optimization 2

Example 2 is an extension of example 1 by adding one more entry to the database:

TABLE 3

Material database

| Material | Parameter $x_1$ | Parameter $x_2$ | Probability that the material to be tested is this entry |
|---|---|---|---|
| $M_1$ | a | c | $P_1$ |
| $M_2$ | b | c | $P_2$ |
| $M_3$ | a | d | $P_3$ |
| $M_4$ | a | e | $P_4$ |

In this case the cost functions are: $K_1=P_2 \cdot c_1(P_1+P_3+P_4)(c_1+c_2)$, and $K_2=(P_3+P_4) \cdot c_2+(P_1+P_2)(c_1+c_2)$.

If one assumes that all the materials are equally probable and the cost of the $MSRM_1$ is equal to the cost of $MSRM_2$, i.e. $P_1=P_2=P_3=P_4=P$, $c_1=c_2=c$, then $K_1=7 \cdot P \cdot c$ and $K_2=6 \cdot P \cdot c$, meaning that the strategy 2 is more efficient (compare to the specific case 1).

If one also assumes that the materials are characterized by three parameters: $x_1$, $x_2$, and $x_3$, then one will have 3 different measurements, see the table 4.

TABLE 4

Measurement cost

| Measurement | Cost |
|---|---|
| $MSRM_1$, parameter $x_1$ | $c_1$ |
| $MSRM_2$, parameter $x_2$ | $c_2$ |
| $MSRM_3$, parameter $x_3$ | $c_3$ |

In this case one has 6 possible strategies: $S_1=\{MSRM_1, MSRM_2, MSRM_3\}$; $S_2=\{MSRM_1, MSRM_3, MSRM_2\}$; $S_3=\{MSRM_2, MSRM_1, MSRM_3\}$; $S_4=\{MSRM_2, MSRM_3, MSRM_1\}$; $S_5=\{MSRM_3, MSRM_1, MSRM_2\}$; and $S_6=\{MSRM_3, MSRM_2, MSRM_1\}$ Using the approach described before one can calculate aggregate cost for each strategy—$K_1$, $K_2$, $K_3$, $K_4$, $K_5$, $K_6$—and decide which will be the first measurement. After selecting the best strategy (say, for example, $S_5$) and making the first measurement according to the selected strategy ($MSRM_3$, in our example), we remove this measurement from the table of measurements, recalculate the probabilities in the database table, and select the new best strategy, i.e. $\{MSRM_1, MSRM_2\}$ or $\{MSRM_2, MSRM_1\}$, using the same approach comparing the average cost of the strategy. (In the case of N measurements, there are N! possible strategies.)

C. Computing Environment

This section describes an example of a computing environment suitable for implementing the technologies described herein.

Figure 6:
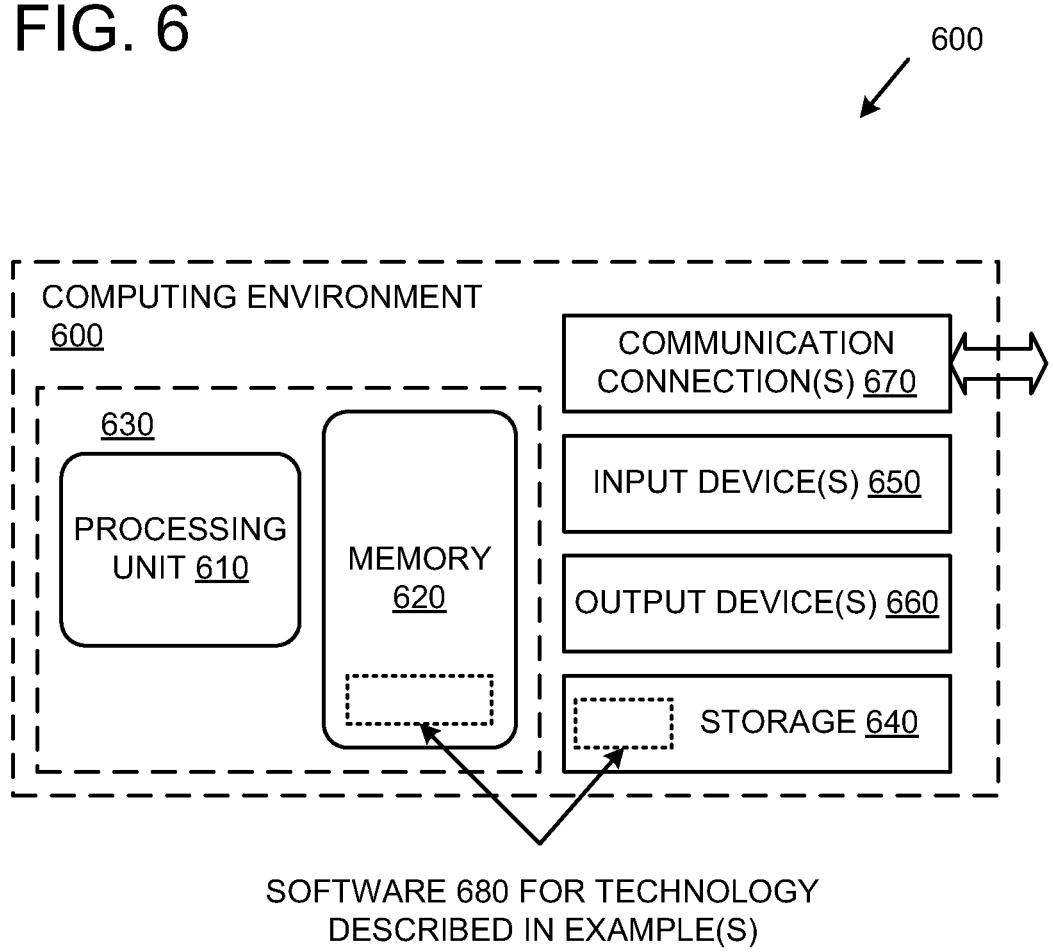
FIG. 6 is a diagram illustrating an example of a computing environment that can be used to implement any of the technologies described herein.

FIG. 6 illustrates a generalized example of a suitable computing environment 600 in which described embodiments, techniques, and technologies may be implemented. The computing environment 600 is not intended to suggest any limitation as to scope of use or functionality of the technology, as the technology may be implemented in diverse general-purpose or special-purpose computing environments. For example, the disclosed technology may be implemented with other computer system configurations, including hand held devices, multiprocessor systems (e.g., one of which could be a cryptographic processor), microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 6, the computing environment 600 can include at least one central processing unit 610 and memory 620. In FIG. 6, this basic configuration 630 is included within a dashed line. The central processing unit 610 executes computer-executable instructions and may be a real or a virtual processor. In a multi-processing system, multiple processing units execute computer-executable instructions to increase processing power and as such, multiple processors can be running simultaneously. The memory 620 may be volatile memory (e.g., registers, cache, RAM), non-volatile memory (e.g., ROM, EEPROM, flash memory, etc.), or some combination of the two. The memory 620 stores software 680 that can, for example, implement the technologies described herein. A computing environment may have additional features. For example, the computing environment 600 can include storage 640, one or more input devices 650, one or more output devices 660, and one or more communication connections 670. An interconnection mechanism (not shown) such as a bus, a controller, or a network, interconnects the components of the computing environment 600. Typically, operating system software (not shown) provides an operating environment for other software executing in the computing environment 600, and coordinates activities of the components of the computing environment 600.

The computer-readable storage 640 may be removable or non-removable media, and includes magnetic disks, magnetic tapes or cassettes, CD-ROMs, CD-RWs, DVDs, or any other tangible medium which can be used to store information and which can be accessed within the computing environment 600. The storage 640 stores instructions for the software 680, which can implement technologies described herein.

The input device(s) 650 may be a touch input device, such as a smartphone or tablet screen, keyboard, keypad, mouse, pen, or trackball, a voice input device, a scanning device, or another device, that provides input to the computing environment 600. For audio, the input device(s) 650 may be a sound card or similar device that accepts audio input in analog or digital form, or a CD-ROM reader that provides audio samples to the computing environment 600. The output device(s) 660 may be a display, printer, speaker, CD-writer, or another device that provides output from the computing environment 600.

The communication connection(s) 670 enable communication over a communication medium (e.g., a connecting network) to another computing entity. The communication medium conveys information such as computer-executable instructions, compressed graphics information, or other data in a modulated data signal.

Alternatives and Variations

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable media (tangible computer-readable storage media, such as one or more optical media discs, volatile memory components (such as DRAM or SRAM), or non-volatile memory components (such as hard drives)) and executed on a computing device (e.g., any commercially available computer, including smart phones or other mobile devices that include computing hardware). By way of example, computer-readable media include memory 620 and/or storage 640. As should be readily understood, the term computer-readable media does not include communication connections (e.g., 670) such as modulated data signals.

Any of the computer-executable instructions for implementing the disclosed techniques as well as any data created and used during implementation of the disclosed embodiments can be stored on one or more computer-readable media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computing device to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Figure 7:
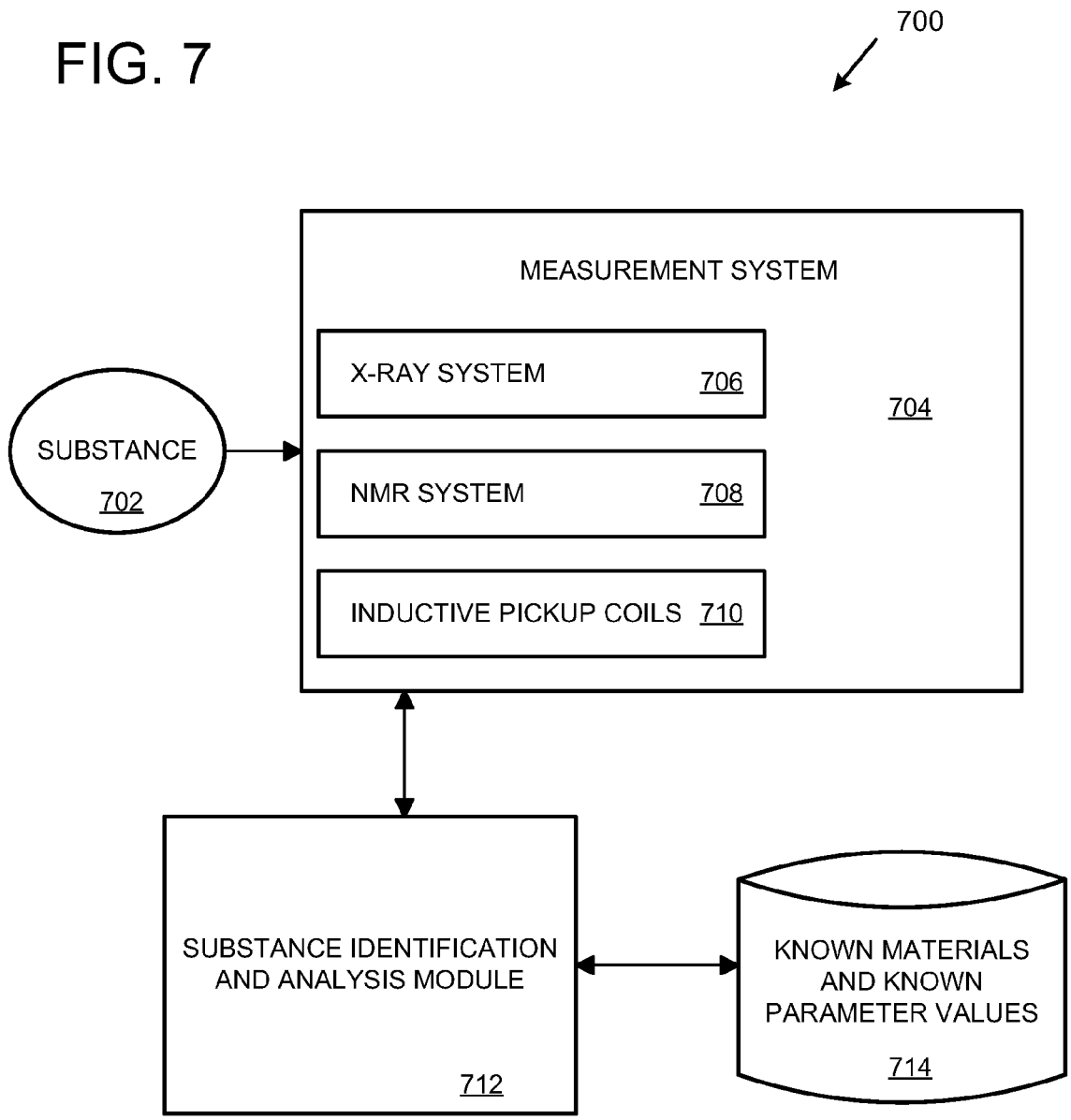
FIG. 7 is a diagram illustrating an example of a substance identification system that can be used to implement any of the technologies described herein.

FIG. 7 illustrates an example substance identification system 700. Substance 702 is analyzed by a measurement system 704. Measurement system 704 contains subsystems for performing various types of measurements, including x-ray system 706, NMR system 708, and inductive pickup coils 710. In some examples, inductive pickup coils 710 are considered to be part of NMR system 708. Substance identification and analysis module 712 is in communication with measurement system 704 and known parameter values for known materials 714, which may be stored as a database, list, or other format. In some examples, measurements conducted by measurement system 704 and subsystems 706, 708, and 710, are controlled by substance and identification analysis module 712. Computing environment 600 may be distributed across measurement system 704, substance identification and analysis module 712 and known materials and known parameter values 714. System 700 may be used to implement the various technologies described herein.

The foregoing description of the preferred embodiments of the invention has been presented for purposes of illustration and description and is not intended to be exhaustive or to limit the claimed invention to the precise form disclosed. Those of skill in the art will readily appreciate that many modifications and variations to the claimed invention are possible in light of the above teaching. The preferred embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined exclusively by the following claims.

What is claimed is:

1. A method of determining the identity of a substance, implemented at least in part by a computing device, the method comprising:
    obtaining an ultra-low field nuclear magnetic resonance (NMR) measurement of a substance;
    determining a volume of the substance;
    determining a relative nuclear susceptibility (RNS) value based at least in part on the obtained NMR measurement and the determined volume, RNS representing density of hydrogen nuclei present in the substance relative to density of hydrogen nuclei present in water; and
    comparing the determined RNS value for the substance to RNS values of known materials in a reference group to determine whether the substance is one of the known materials.

2. The method of claim 1, wherein the comparing step includes searching a list of the known materials and corresponding RNS values.

3. The method of claim 1, wherein the known materials in the reference group are hazardous materials.

4. The method of claim 1, further comprising outputting a result.

5. The method of claim 4, wherein the result is one of an identification of the substance as a known material in the reference group or a determination that the substance is not one of the known materials in the reference group.

6. The method of claim 1, wherein the volume is determined at least in part by analyzing an x-ray image of the sample.

7. The method of claim 1, wherein the volume is determined at least in part through analysis of current induced in each of two substantially concentric coils in response to magnetization of the substance.

8. The method of claim 7, wherein the analysis comprises determining a ratio of the current induced in a first of the two substantially concentric coils and the current induced in a second of the two substantially concentric coils, and wherein the determined ratio is indicative of the volume of the substance.

9. A method of determining the identity of a substance, implemented at least in part by a computing device, the method comprising:
    obtaining an ultra-low field nuclear magnetic resonance (NMR) measurement of a substance;
    analyzing the NMR measurement to determine a value of at least one classification parameter comprising one of $T_1$, $T_2$, and $T_{1\rho}$;
    determining a value of at least one additional classification parameter comprising: one of
        a relative nuclear susceptibility (RNS) of the substance based at least in part on the obtained NMR measurement and a determined volume, RNS representing the density of hydrogen nuclei present in the substance relative to the density of hydrogen nuclei present in water; and
        an x-ray linear attenuation coefficient (LAC) of the substance; and
    comparing the values of the at least one classification parameter and the at least one additional classification parameter to classification parameter values of known materials in a reference group to determine whether the substance is one of the known materials.

10. The method of claim 9, wherein the comparing step includes searching a list of known materials and corresponding classification parameter values.

11. The method of claim 9, wherein the known materials in the reference group are hazardous materials.

12. The method of claim 9, further comprising outputting a result.

13. The method of claim 12, wherein the result is one of an identification of the substance as a known material in the reference group or a determination that the substance is not one of the known materials in the reference group.

14. The method of claim 9, wherein the at least one additional classification parameter comprises LAC.

15. The method of claim 9, wherein the at least one additional classification parameter comprises RNS.

16. The method of claim 15, wherein the volume is determined at least in part by analyzing an x-ray image of the sample.

17. The method of claim 15, wherein the volume is determined at least in part through analysis of current induced in each of two substantially concentric coils in response to magnetization of the substance.

18. The method of claim 17, wherein the analysis comprises determining a ratio of the current induced in a first of the two substantially concentric coils and the current induced in a second of the two substantially concentric coils, and wherein the determined ratio is indicative of the volume of the substance.

* * * * *